(12) United States Patent
Wu

(10) Patent No.: US 8,899,097 B2
(45) Date of Patent: Dec. 2, 2014

(54) AIRBORNE IMPURITIES DETECTION

(75) Inventor: Tateh Wu, Seattle, WA (US)

(73) Assignee: The Boeing Company, Chicago, IL (US)

( * ) Notice: Subject to any disclaimer, the term of this patent is extended or adjusted under 35 U.S.C. 154(b) by 338 days.

(21) Appl. No.: 13/275,575

(22) Filed: Oct. 18, 2011

(65) Prior Publication Data
US 2013/0091928 A1  Apr. 18, 2013

(51) Int. Cl.
| | | |
|---|---|---|
| G01N 37/00 | (2006.01) | |
| G01N 21/53 | (2006.01) | |
| G08B 17/103 | (2006.01) | |
| G01N 21/27 | (2006.01) | |
| G08B 29/20 | (2006.01) | |

(52) U.S. Cl.
CPC ............ G01N 21/534 (2013.01); G08B 17/103 (2013.01); G01N 21/274 (2013.01); G08B 29/20 (2013.01)
USPC ....................................................... 73/28.01

(58) Field of Classification Search
None
See application file for complete search history.

(56) References Cited

U.S. PATENT DOCUMENTS

| | | | | |
|---|---|---|---|---|
| 2,604,597 | A * | 7/1952 | Cahusac et al. ................ | 250/204 |
| 2,627,064 | A * | 1/1953 | Allen ............................. | 340/515 |
| 3,524,707 | A | 8/1970 | Hansen | |
| 4,185,278 | A * | 1/1980 | Lintelmann et al. .......... | 340/630 |
| 4,870,394 | A * | 9/1989 | Corl et al. ..................... | 340/630 |
| 4,883,972 | A * | 11/1989 | Coe ................................ | 250/575 |
| 5,486,810 | A * | 1/1996 | Schwarz ....................... | 340/521 |
| 5,777,748 | A * | 7/1998 | Stengel ......................... | 356/438 |
| 5,791,982 | A | 8/1998 | Curry | |
| 6,111,511 | A * | 8/2000 | Sivathanu et al. ............ | 340/577 |
| 6,377,183 | B1 | 4/2002 | Baker et al. | |
| 6,975,237 | B2 | 12/2005 | Barton et al. | |
| 7,154,388 | B2 | 12/2006 | Mazzone | |
| 7,688,199 | B2 | 3/2010 | Zhang et al. | |
| 7,849,931 | B2 | 12/2010 | Ng | |
| 2005/0253730 | A1 | 11/2005 | Ropke | |
| 2006/0152726 | A1* | 7/2006 | Larsen et al. ................. | 356/416 |

FOREIGN PATENT DOCUMENTS

| | | | |
|---|---|---|---|
| GB | 1390227 | | 4/1975 |
| JP | 360100034 | * | 6/1985 |
| WO | 9954700 A2 | | 10/1999 |

OTHER PUBLICATIONS

European Search Report Application No. 12188126.2-2208, Feb. 5, 2013.

* cited by examiner

*Primary Examiner* — Robert R Raevis
(74) *Attorney, Agent, or Firm* — Toler Law Group, PC

(57) ABSTRACT

Systems and methods for detection of airborne impurities in confined spaces are disclosed. In one embodiment, a detection system to detect impurities in a confined chamber comprises an emitter to emit radiation, at least one channel positioned proximate the emitter to receive radiation from the emitter at a first end of the channel, and a receiver positioned proximate a second end of the channel to receive radiation from the emitter, and generate a first signal in response to the radiation received from the emitter. Other embodiments may be described.

14 Claims, 5 Drawing Sheets

AIRBORNE IMPURITIES DETECTION

BACKGROUND

The subject matter described herein relates to detection of airborne impurities and sensor systems for detection of airborne impurities in vehicles such as aircraft.

Detectors may be used to detect the presence of airborne impurities. By way of example, smoke detectors may be used to detect the presence of smoke particles or aerosols in the air. Smoke detection in vehicle such as aircraft may be particularly challenging due to variations in configurations between aircraft cabin and turbulence in the cabin air created by air conditioning and air pressure management systems. Thus, systems and methods to detect airborne impurities in confined chambers such as, e.g., aircraft cabins may find utility.

SUMMARY

In one embodiment, a detection system to detect impurities in a confined chamber comprises an emitter to emit radiation, at least one channel positioned proximate the emitter to receive radiation from the emitter at a first end of the channel, and a receiver positioned proximate a second end of the channel to receive radiation from the emitter, and generate a first signal in response to the radiation received from the emitter In another embodiment, an aircraft comprises a fuselage defining at least one confined chamber, a detection system to detect impurities in a confined chamber, comprising an emitter to emit radiation, at least one channel positioned proximate the emitter to receive radiation from the emitter at a first end of the channel, and a receiver positioned proximate a second end of the channel to receive radiation from the emitter, and generate a first signal in response to the radiation received from the emitter.

In another embodiment, a method to detect impurities in a confined chamber comprises emitting radiation from an emitter into a first end of at least at least one channel, receiving radiation from the emitter in a receiver at a second end of the at least one channel, and generating a first signal in response to the radiation received from the emitter.

Further areas of applicability will become apparent from the description provided herein. It should be understood that the description and specific examples are intended for purposes of illustration only and are not intended to limit the scope of the present disclosure

BRIEF DESCRIPTION OF THE DRAWINGS

Embodiments of methods and systems in accordance with the teachings of the present disclosure are described in detail below with reference to the following drawings.

DETAILED DESCRIPTION

Configurations for systems and methods to detect airborne impurities such as, for example, smoke, in a confined chamber are described herein. Specific details of certain embodiments are set forth in the following description and the associated figures to provide a thorough understanding of such embodiments. One skilled in the art will understand, however, that alternate embodiments may be practiced without several of the details described in the following description.

The invention may be described herein in terms of functional and/or logical block components and various processing steps. For the sake of brevity, conventional techniques related to data transmission, signaling, network control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

The following description may refer to components or features being "connected" or "coupled" or "bonded" together. As used herein, unless expressly stated otherwise, "connected" means that one component/feature is in direct physically contact with another component/feature. Likewise, unless expressly stated otherwise, "coupled" or "bonded" means that one component/feature is directly or indirectly joined to (or directly or indirectly communicates with) another component/feature, and not necessarily directly physically connected. Thus, although the figures may depict example arrangements of elements, additional intervening elements, devices, features, or components may be present in an actual embodiment.

Figure 1:
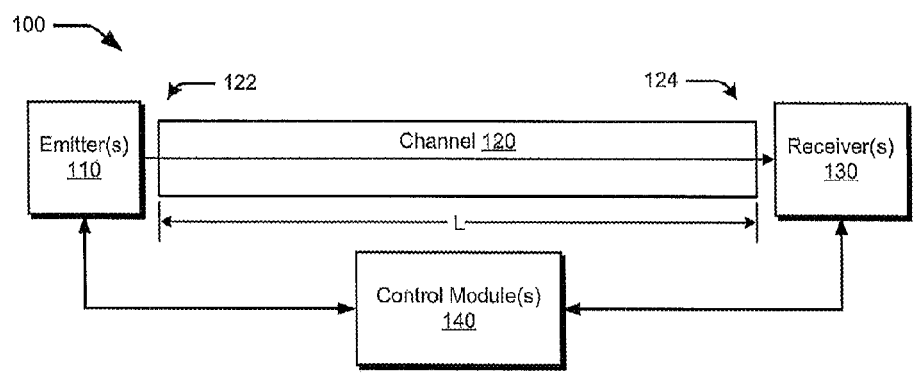
FIG. 1 is a schematic, high-level illustration of a system to detect airborne impurities, according to embodiments.

FIG. 1 is a schematic top-view of a system 100 to detect impurities in a confined chamber. In the embodiment depicted in FIG. 1, the system 100 comprises one or more emitter 110 to emit radiation, at least one channel 120 positioned proximate the emitter(s) 110 to receive radiation from the emitter(s) 110 at a first end 122 of the channel 120, and one or more receivers 130 positioned proximate a second end 124 of the channel 120. The receiver(s) 130 receive radiation from the emitter(s) 110 and generate a first signal in response to the radiation received from the emitter 110. A control module 140 may be coupled to the emitter(s) 110 and the receiver(s) 130.

Emitter (s) 110 may be embodied as conventional radiation emitter(s) such as, for example, light emitting diodes (LEDs) or the like. In some embodiments emitter(s) 110 emit radiation in the visible spectrum, i.e., light. The radiation may be in a narrow frequency width such that the radiation is a single color to the naked eye. Emitter(s) 110 may comprise one or more collimators to collimate radiation emitted therefrom, and one or more lens assemblies to focus the radiation into a directional beam. In alternate embodiments the emitter(s) 110 may emit radiation outside the visible spectrum or may emit incoherent radiation, at least a portion of which may be visible as white light.

Receiver(s) 130 may comprise a detector such as a photodiode or the like to detect radiation levels incident on an input of receiver(s) 130 and generate a signal representative of the level of radiation. By way of example, in some embodiments receiver(s) 130 generate an electrical signal having a voltage which is proportional to the level of radiation incident on receiver(s) 130.

In the system 100 depicted in FIG. 1 the emitter(s) 110 and the receiver(s) 130 are coupled to one or more control module(s) 140, which includes control logic to manage operations of the system 100. In some embodiments control module(s) 140 may be embodied as, or may include, one or more processor-based controllers and may implement operations including initialization, calibration, power management, and data monitoring and collection. Various structural and functional aspect of control module(s) 140 are described in greater detail below.

In the embodiment depicted in FIG. 1 the emitter(s) 110 are arranged such that radiation output from the emitter(s) 110 is directed into a channel 120 and the receiver(s) 130 are positioned to receive radiation from channel(s) 120. In the embodiment depicted in FIG. 1 the channel 120 has a length indicated by the reference L. The specific length L of the channel 120 is not critical to the invention and may be a function of the dimensions of the confined chamber in which a system 100 is installed. In general, the length L may vary from a few inches to tens or hundreds of feet. In general, channel 120 isolates airborne particles or aerosols from air turbulence in a confined chamber, which enables the system to obtain more accurate and stable readings of airborne particle concentration in the environment between the emitter(s) 110 and the receiver(s) 130.

Figure 2A:
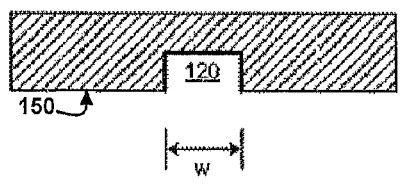
FIGS. 2A-2F are schematic side cross-sectional view of channels which may be used in a system to detect airborne impurities, according to embodiments.
Figure 2B:
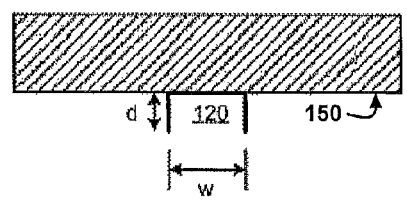

FIGS. 2A-2F are schematic side cross-sectional view of channels which may be used in a system to detect airborne impurities, according to embodiments. Referring first to FIG. 2A, in some embodiments the channel 120 may be integrated into a surface 150 of a compartment. Alternately, as illustrated in FIG. 2B, the channel 120 may be mounted on a surface 150 of a compartment. The channel 120 may have a width indicated by reference w in FIGS. 2A-2F that measures between 0.25 inches and 3.00 inches, and a depth that measures between 0.25 inches and 3.00 inches. One skilled in the art will recognize, however, that the particular dimensions of the channel are not critical, provided that the channel is dimensioned to reduce turbulent airflow in the volume defined by the channel 120 and at the same time retain airborne impurities in the channel 120.

Figure 2C:
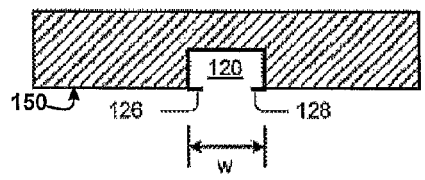
Figure 2D:
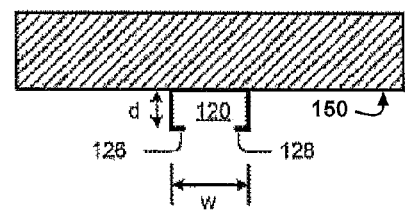

Referring to FIGS. 2C-2D, in some embodiments a channel 120 may comprise one or more lips 126, 128 that depend from the sides of the channel 120 to reduce turbulent airflow from the compartment into the channel 120. Again, the specific dimensions of the lips are not critical, provided that the lip is dimensioned to reduce turbulent airflow in the volume defined by the channel 120 and at the same time retain airborne impurities in the channel 120. In some embodiments the lips 126, 128 measure between 0.06 inches and 1.00 inches.

Figure 2E:
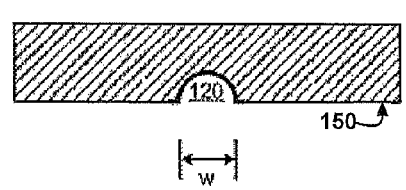
Figure 2F:
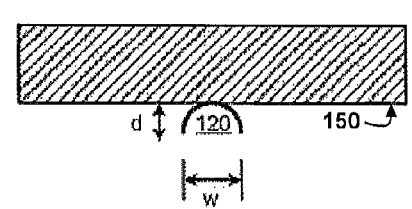

While the channel 120 depicted in FIGS. 2A-2D is substantially rectangular in cross-section, the specific configuration of the cross-sectional shape is not critical. Referring to FIGS. 2E and 2F, in some embodiments the channel 120 is substantially semicircular in cross-section. Other cross-sectional shapes may be implemented and channels 120 of varying shapes may include lips 126, 128 as depicted in FIGS. 2C-2D.

Figure 3:
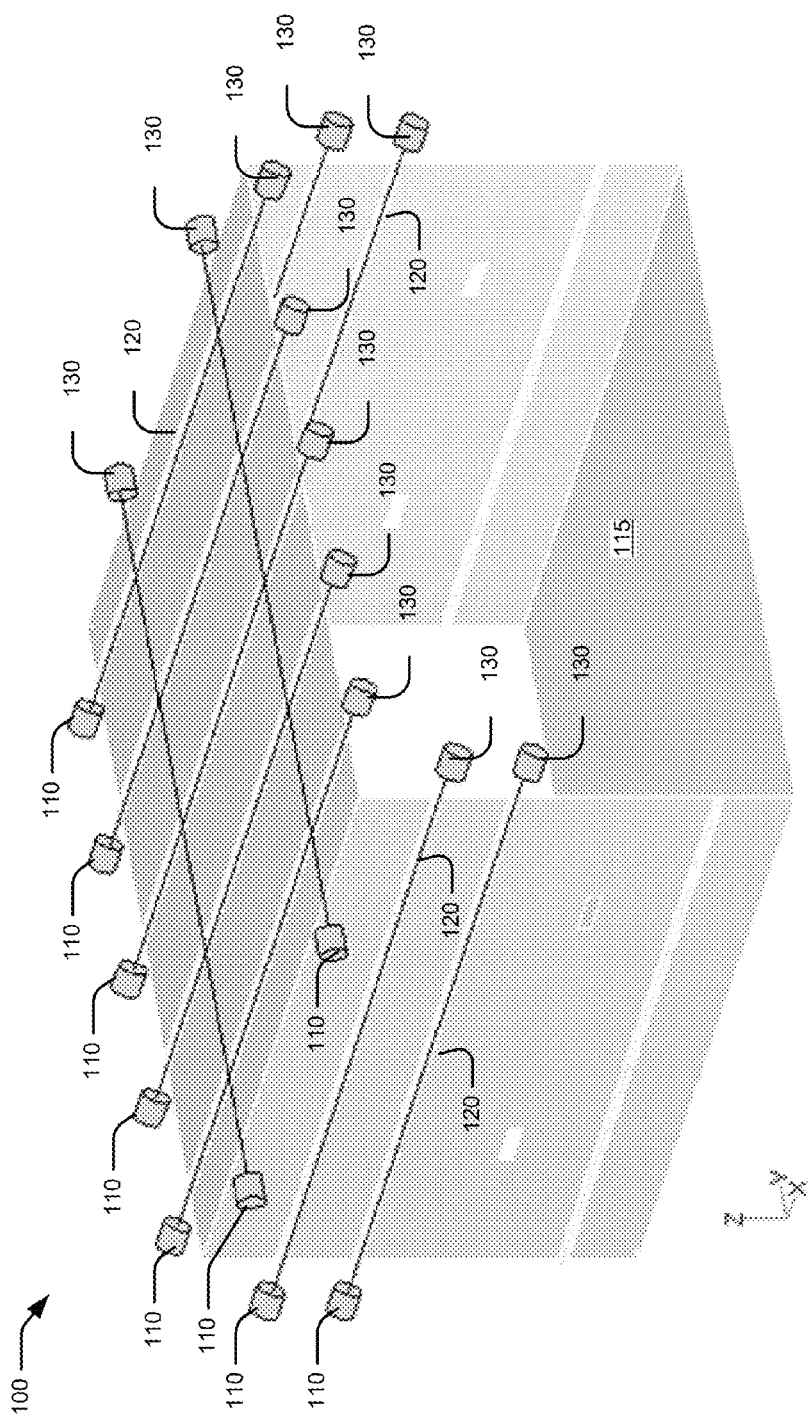
FIG. 3 is a schematic perspective view of a system to detect airborne impurities, according to embodiments.

FIG. 3 is a schematic perspective view of a system 100 to detect airborne impurities in a confined chamber 115, according to embodiments. In some embodiments the chamber 115 may comprise a confined compartment in a vehicle such as, e.g., a storage or passenger compartment in an aircraft or other vehicle. In the embodiment depicted in FIG. 3 a plurality of channels 120 are formed in or mounted to surfaces of the chamber 115. A corresponding plurality of emitters 110 are positioned to direct radiation into the channels 120 and a corresponding plurality of receivers 130 are positioned to receive the radiation from the channels 120. As indicated in FIG. 1, the emitters 110 and receivers 130 may be coupled to one or more control modules 150. The emitters 110, channels 120, and receivers 130 form a system 100 capable of monitoring for airborne impurities in the compartment 115. Unlike conventional point-source monitoring systems which can only detect impurities at the point source, the system 100 is capable of detecting impurities anywhere along the extents of the channels 120.

Figure 4:
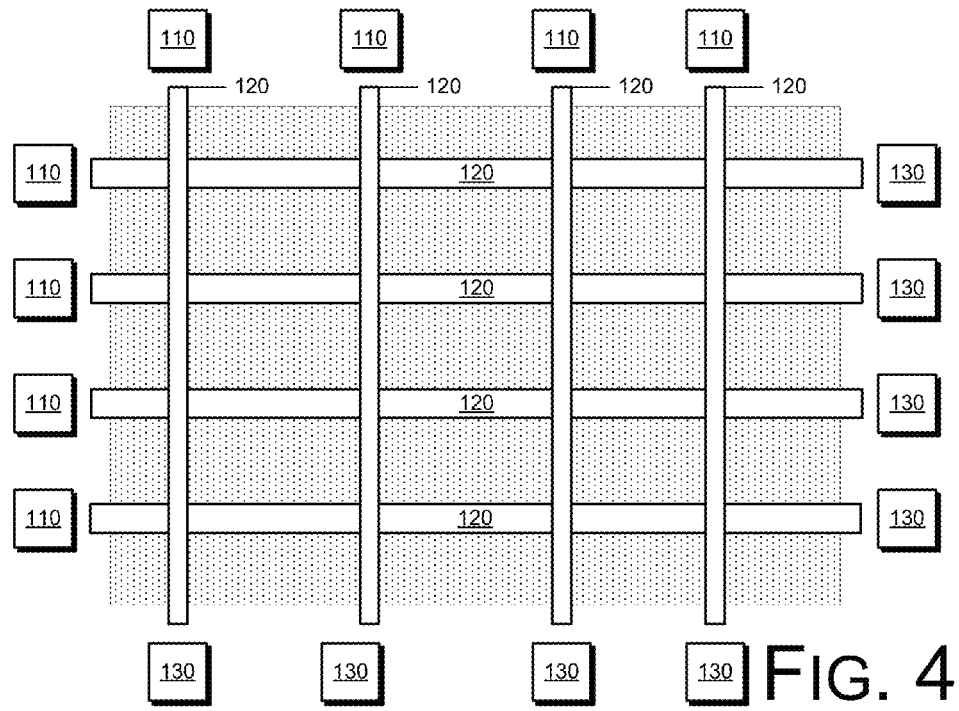
FIG. 4 is a schematic top view of a system to detect airborne impurities, according to embodiments.

In some embodiments a system 100 may be designed such that there is a 1:1 correspondence between emitters 110 and receivers 130. FIG. 4 is a schematic top view of a system to detect airborne impurities, according to embodiments in which there is a 1:1 correspondence between emitters 110 and receivers 130.

Figure 5:
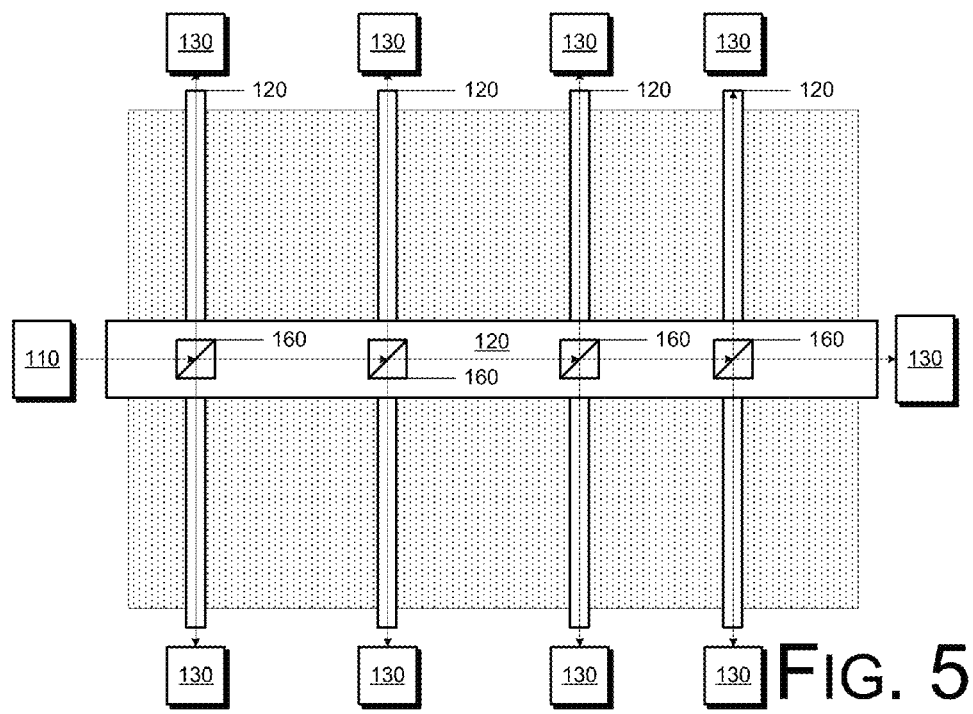
FIG. 5 is a schematic top view of a system to detect airborne impurities, according to embodiments.

In alternate embodiments there may be a 1:n relationship between emitters 110 and receivers 130. FIG. 5 is a schematic top view of a system to detect airborne impurities, according to embodiments in which there is a 1:n correspondence between emitters 110 and receivers 130. Referring to FIG. 5, in some embodiments radiation from an emitter 110 may be directed along a channel 120 which includes one or more beam splitter assemblies 160. Beam splitter assemblies 160 split the radiation incident on the beam splitter assembly 160 in to a first component which is directed to a first receiver 130, a second component which is directed to a second receiver 130, and a third component which is transmitted through the beam splitter assembly 160. Multiple beam splitter assemblies 160 may be positioned in series along the channel 120 to feed radiation to a plurality of receivers 130.

Figure 6:
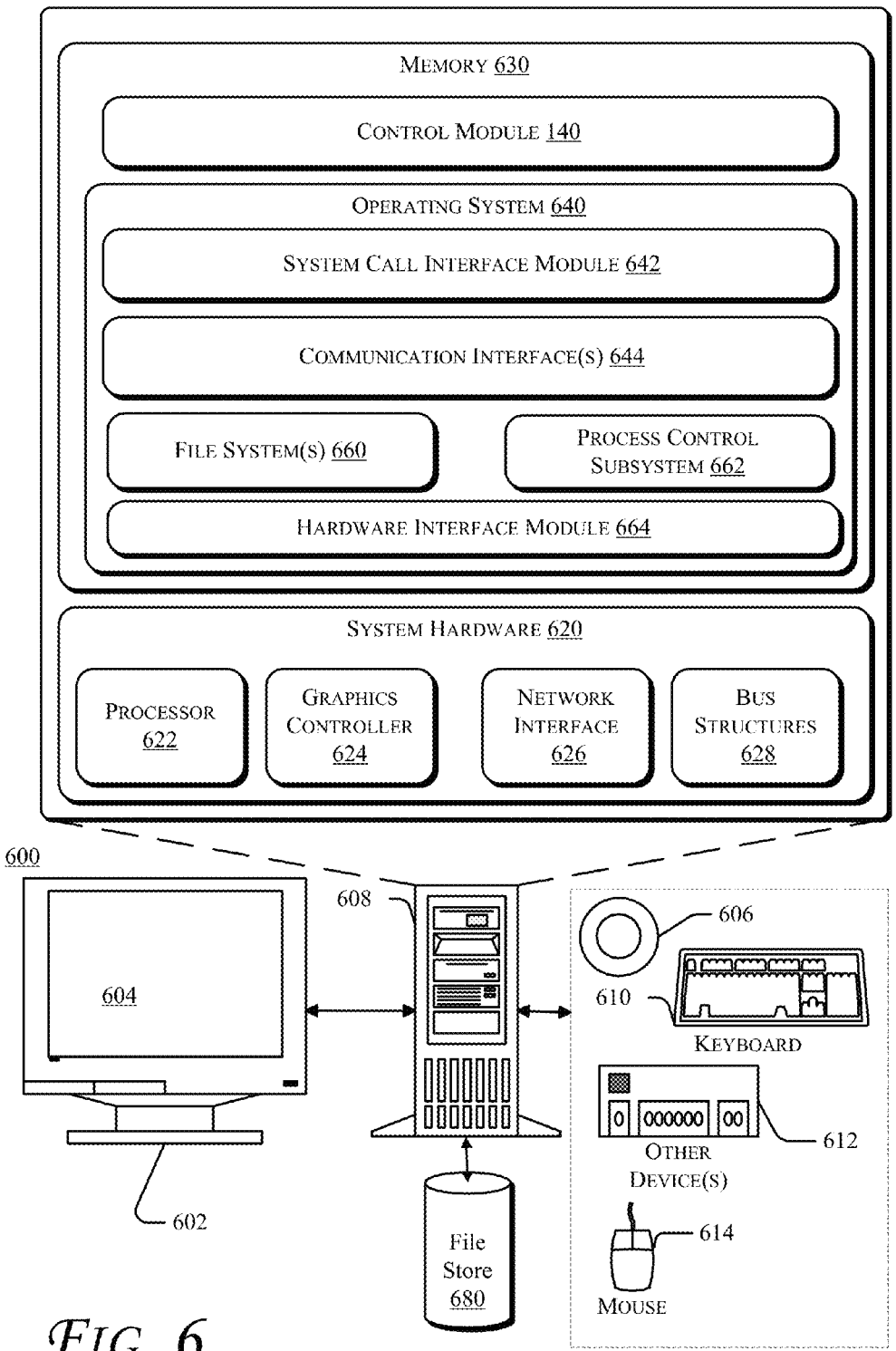
FIG. 6 is a schematic illustration of a computing device, according to embodiments.

As described above, the emitter(s) 110 and the receiver(s) 130 may be coupled to a control module 140. In some embodiments the control module 140 may be implemented as a logic module in a general purpose computing system. In a networked, computer-based system one or more of the computer systems include a control module 140 adapted to implement the control operations described with reference to FIG. 6. FIG. 6 is a schematic illustration of a computing system 600 that may be used to monitor for airborne impurities. In some embodiments, system 600 includes a computing device 608 and one or more accompanying input/output devices including a display 602 having a screen 604, one or more speakers 606, a keyboard 610, one or more other I/O device(s) 612, and a mouse 614. The other I/O device(s) 612 may include a touch screen, a voice-activated input device, a track ball, and any other device that allows the system 600 to receive input from a user.

The computing device 608 includes system hardware 620 and memory 630, which may be implemented as random access memory and/or read-only memory. A file store 680 may be communicatively coupled to computing device 608. File store 680 may be internal to computing device 608 such as, e.g., one or more hard drives, CD-ROM drives, DVD-ROM drives, or other types of storage devices. File store 680 may also be external to computer 608 such as, e.g., one or more external hard drives, network attached storage, or a separate storage network.

System hardware 620 may include one or more processors 622, video controllers 624, network interfaces 626, and bus structures 628. In one embodiment, processor 622 may be embodied as an Intel® Pentium IV® processor available from Intel Corporation, Santa Clara, Calif., USA. As used herein, the term "processor" means any type of computational element, such as but not limited to, a microprocessor, a microcontroller, a complex instruction set computing (CISC) microprocessor, a reduced instruction set (RISC) microprocessor, a very long instruction word (VLIW) microprocessor, or any other type of processor or processing circuit.

Graphics controller 624 may function as an adjunction processor that manages graphics and/or video operations. Graphics controller 624 may be integrated onto the motherboard of computing system 600 or may be coupled via an expansion slot on the motherboard.

In one embodiment, network interface 626 could be a wired interface such as an Ethernet interface (see, e.g., Institute of Electrical and Electronics Engineers/IEEE 802.3-2002) or a wireless interface such as an IEEE 802.11a, b or g-compliant interface (see, e.g., IEEE Standard for IT-Telecommunications and information exchange between systems LAN/MAN—Part II: Wireless LAN Medium Access Control (MAC) and Physical Layer (PHY) specifications Amendment 4: Further Higher Data Rate Extension in the 2.4 GHz Band, 802.11G-2003). Another example of a wireless interface would be a general packet radio service (GPRS) interface (see, e.g., Guidelines on GPRS Handset Requirements, Global System for Mobile Communications/GSM Association, Ver. 3.0.1, December 2002).

Bus structures 628 connect various components of system hardware 628. In one embodiment, bus structures 628 may be one or more of several types of bus structure(s) including a memory bus, a peripheral bus or external bus, and/or a local bus using any variety of available bus architectures including, but not limited to, 11-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Universal Serial Bus (USB), Advanced Graphics Port (AGP), Personal Computer Memory Card International Association bus (PCMCIA), and Small Computer Systems Interface (SCSI).

Memory 630 may include an operating system 640 for managing operations of computing device 608. In one embodiment, operating system 640 includes a hardware interface module 654 that provides an interface to system hardware 620. In addition, operating system 640 may include a file system 650 that manages files used in the operation of computing device 608 and a process control subsystem 652 that manages processes executing on computing device 608. Further, memory module 630 may comprise an evaluation module 660 to implement the analysis operations described with reference to FIG. 2.

Operating system 640 may include (or manage) one or more communication interfaces that may operate in conjunction with system hardware 620 to transceive data packets and/or data streams from a remote source. Operating system 640 may further include a system call interface module 642 that provides an interface between the operating system 640 and one or more application modules resident in memory 630. Operating system 640 may be embodied as a UNIX operating system or any derivative thereof (e.g., Linux, Solaris, etc.) or as a Windows® brand operating system, or other operating systems.

In one embodiment, memory 630 includes a control module 140 to manage operations of the system 100. The control module 140 may include logic instructions encoded in a computer-readable storage medium which, when executed by processor 622, cause the processor 622 to activate, calibrate, and manage the system 100 to detect impurities in a confined chamber.

Figure 7:
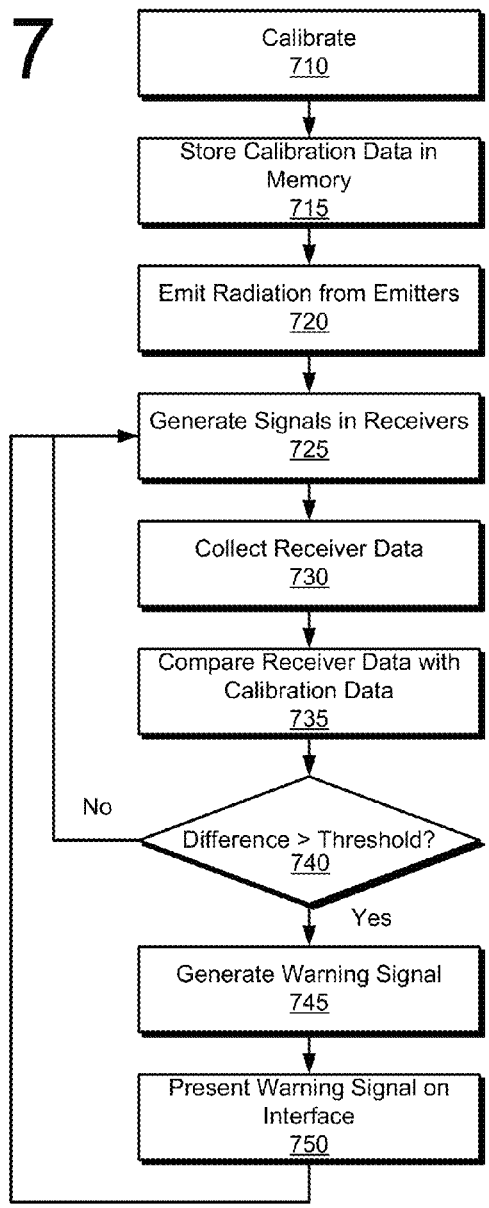
FIG. 7 is a flowchart illustrating operations in a method detect airborne impurities, according to embodiments.
Figure 8:
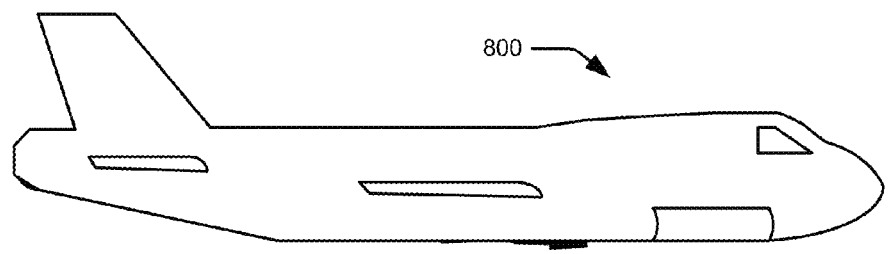
FIG. 8 is a schematic illustration of an aircraft, according to embodiments.

FIG. 7 is a flowchart illustrating operations in a method detect airborne impurities, according to embodiments. Referring to FIG. 7, at operation 710 a calibration procedure may be implemented. In some embodiments a calibration procedure may include activating the system when the atmosphere in the confined chamber is in normal operating conditions and free from evens such as, e.g., fire, which might generate airborne impurities in the chamber. Appropriate power levels may be established for the emitter(s) 110 and output signals from the receiver(s) 130 may be collected and stored (operation 715) in a suitable memory location, e.g., in the memory 630 or the file store 680 associated with the computing system 600.

Once the system 100 is calibrated it may be activated for operation. In use, the system 100 may be operated continuously or may be operated intermittently. For example, the system 100 may be activated at periodic intervals and data may be collected during the intervals of activation. Whatever mode of operation is selected, at operation 720 the emitters 110 are activated and radiation is emitted from the emitters 110. At operation 725 the receivers 130 receive the radiation and generate signals in response thereto. In some embodiments the output signal from the receiver(s) 130 is proportional to the radiation received. Thus, when the air in the confined chamber is substantially free of airborne impurities such as smoke the signal generated by the receiver(s) 130 should approximate the signal generated during the calibration process. By contrast, in the event a fire or other event disburses airborne impurities in the air of the confined chamber 115, the airborne impurities will reduce the radiation levels that impinge upon the receivers(s) 130, and therefore the output signal of the receiver(s) 130.

At operation 730 receiver data is collected and at operation 735 receiver data is compared with the data collected during the calibration process. If, at operation 740, the difference between the collected data and the calibration data does not exceed a threshold then control passes back to operation 725 and the system may continue normal operations monitoring for airborne impurities.

By contrast, if at operation 740 the difference exceeds a threshold then control passes to operation 745 and a warning signal is generated, which signal may be presented on a user interface at operation 750. By way of example, the warning signal may be presented on a visual display, an auditory display, or combinations thereof.

In some embodiments a system 100 may be incorporated into compartments of on an aircraft 800, such as an airplane, helicopter, spacecraft or the like. In alternate embodiments a system 100 may be incorporated into a ground-based vehicle such as a truck, tank, train, or the like, or on a water-based vehicle such as a ship. In further embodiments a system 100 may be incorporated into a land-based communication station.

While various embodiments have been described, those skilled in the art will recognize modifications or variations which might be made without departing from the present disclosure. The examples illustrate the various embodiments and are not intended to limit the present disclosure. Therefore, the description and claims should be interpreted liberally with only such limitation as is necessary in view of the pertinent prior art.

What is claimed is:

1. A system to detect impurities in a chamber, the system comprising:
   an emitter to emit radiation;
   a plurality of channels integrated into a surface of the chamber to receive radiation from the emitter;

a plurality of beam splitters to direct radiation from the emitter into the plurality of channels; and a plurality of receivers to:
   receive radiation from the emitter; and
   generate a first plurality of signals in response to the radiation received from the emitter.

2. The system of claim 1, further comprising a control module coupled to the plurality of receivers to:
   receive the first plurality of signals from the plurality of receivers; and
   generate a warning when the first plurality of signals indicates that an impurity in the chamber has exceeded a threshold.

3. The system of claim 1, wherein at least one of the plurality of channels has a substantially semicircular cross-section.

4. The system of claim 1, further comprising a control module configured to generate a warning when a difference between the first plurality of signals and a second plurality of signals satisfies a threshold, wherein the first plurality of signals corresponds to the radiation received from the emitter at a first time, and wherein the second plurality of signals corresponds to the radiation received from the emitter at a second time.

5. An aircraft comprising:
   a fuselage defining at least one chamber;
   a detection system to detect impurities in the at least one chamber, the detection system comprising:
      an emitter to emit radiation;
      a plurality of channels extending along a surface of the at least one chamber to receive radiation from the emitter;
      a plurality of beam splitters to direct radiation from the emitter into the plurality of channels; and
      a plurality of receivers to:
         receive radiation from the emitter; and
         generate a first plurality of signals in response to the radiation received from the emitter.

6. The aircraft of claim 5, further comprising a control module coupled to the plurality of receivers to:
   receive the first plurality of signals from the plurality of receivers; and
   generate a warning when the first plurality of signals indicates that an impurity in the at least one chamber has exceeded a threshold.

7. The aircraft of claim 5, wherein the plurality of channels are integrated into the surface.

8. The aircraft of claim 5, wherein the plurality of channels are mounted onto the surface.

9. The system of claim 5, wherein at least one of the plurality of channels has a substantially semicircular cross-section.

10. The system of claim 5, further comprising a control module configured to generate a warning when a difference between the first plurality of signals and a second plurality of signals satisfies a threshold, wherein the first plurality of signals corresponds to the radiation received from the emitter at a first time, and wherein the second plurality of signals corresponds to the radiation received from the emitter at a second time.

11. A method to detect impurities in a chamber, comprising:
   emitting radiation from an emitter into a plurality of channels integrated into a surface of the chamber, wherein a plurality of beam splitters are used to direct radiation from the emitter into the plurality of channels;
   receiving radiation from the emitter in a plurality of receivers; and
   generating a first plurality of signals in response to the radiation received from the emitter.

12. The method of claim 11, further comprising:
   receiving, at a control module coupled to the plurality of receivers, the first plurality of signals from the plurality of receivers; and
   generating a warning when the first plurality of signals indicates that an impurity in the chamber has exceeded a threshold.

13. The method of claim 11, wherein at least one of the plurality of channels has a substantially semicircular cross-section.

14. The method of claim 11, further comprising generating a warning when a difference between the first plurality of signals and a second plurality of signals satisfies a threshold, wherein the first plurality of signals corresponds to the radiation received from the emitter at a first time, and the second plurality of signals corresponds to the radiation received from the emitter at a second time.

* * * * *